United States Patent
Kumar et al.

(10) Patent No.: US 12,053,543 B2
(45) Date of Patent: Aug. 6, 2024

(54) SUNSCREEN COMPOSITION CONTAINING VISIBLY TRANSPARENT BIOCOMPATIBLE ULTRA VIOLET BLOCKING POLYMER NANOPARTICLES

(71) Applicant: Tata Consultancy Services Limited, Mumbai (IN)

(72) Inventors: Venkiteswaran Sathyavageeswaran Pavan Kumar, Pune (IN); Auhin Kumar Maparu, Pune (IN); Ashish Masarkar, Pune (IN); Beena Rai, Pune (IN)

(73) Assignee: Tata Consultancy Limited Services, Mumbai (IN)

( * ) Notice: Subject to any disclaimer, the term of this patent is extended or adjusted under 35 U.S.C. 154(b) by 197 days.

(21) Appl. No.: 17/813,237

(22) Filed: Jul. 18, 2022

(65) Prior Publication Data
US 2023/0165783 A1    Jun. 1, 2023

(30) Foreign Application Priority Data
Oct. 26, 2021   (IN) .............................. 202121048895

(51) Int. Cl.
| | | |
|---|---|---|
| *A61K 8/893* | (2006.01) | |
| *A61K 8/04* | (2006.01) | |
| *A61K 8/895* | (2006.01) | |
| *A61K 9/51* | (2006.01) | |
| *A61Q 17/04* | (2006.01) | |

(52) U.S. Cl.
CPC ............. *A61K 8/893* (2013.01); *A61K 8/042* (2013.01); *A61K 8/895* (2013.01); *A61K 9/51* (2013.01); *A61Q 17/04* (2013.01)

(58) Field of Classification Search
None
See application file for complete search history.

(56) References Cited

U.S. PATENT DOCUMENTS

2013/0230709 A1*  9/2013  Zhou ................. H01G 11/36
                                                                428/219

FOREIGN PATENT DOCUMENTS

| BR | PI0821690 B1 | 10/2016 |
|---|---|---|
| CN | 1781476 B | 10/2013 |
| EP | 2819643 B1 | 10/2017 |
| ES | 2380626 T3 | 5/2012 |

* cited by examiner

*Primary Examiner* — Nannette Holloman
(74) *Attorney, Agent, or Firm* — Finnegan, Henderson, Farabow, Garrett & Dunner, L.L.P.

(57) ABSTRACT

This disclosure relates generally to a sunscreen composition containing visibly transparent biocompatible ultraviolet blocking polymer nanoparticles. The sunscreen composition comprising polydimethylsiloxane (PDMS) nanoparticles, at least one flavoring agent, at least one coloring agent, at least one stabilizer, and at least one preservative, in a defined form, wherein size of the PDMS nanoparticles ranging from 200 to 1200 nm. The size of the PDMS nanoparticles ranging from 200 to 500 nm for air medium and from 800 to 1200 nm for water medium. The PDMS nanoparticles comprise a PDMS polymer having terminal functional group selected from alkyl, alkoxy, vinyl, hydroxyl, or a combination thereof. The sunscreen composition is available in the defined form selected from a group consisting of a skin cream, a skin lotion, a powder, a gel, and a sprayable liquid.

11 Claims, 4 Drawing Sheets

SUNSCREEN COMPOSITION CONTAINING VISIBLY TRANSPARENT BIOCOMPATIBLE ULTRA VIOLET BLOCKING POLYMER NANOPARTICLES

PRIORITY CLAIM

This U.S. patent application claims priority under 35 U.S.C. § 119 to: Indian Patent Application No. 202121048895, filed on 26 October, 2021. The entire contents of the aforementioned application are incorporated herein by reference.

TECHNICAL FIELD

The disclosure herein generally relates to the field of cosmetics, and, more particularly, to a sunscreen composition containing visibly transparent biocompatible ultraviolet (UV) blocking polymer nanoparticles.

BACKGROUND

Materials used for making a sunscreen composition are generally classified into physical materials and chemical materials. The sunscreen composition made with the physical materials are generally called as physical sunscreens. Similarly, the sunscreen composition made with the chemical materials are generally called as chemical sunscreens. The chemical sunscreens available in the market are generally organic compounds that attenuate ultraviolet (UV) radiation purely by absorption at the molecular level. Studies indicate that most of the known chemical sunscreens (compounds) have potentially toxic effects on skin cells.

The physical sunscreens available in the market are mostly made of mineral nano particles which attenuate UV through their properties of scattering and reflection in addition to absorption. The physical sunscreens are preferred over the chemical sunscreens due to adverse effects of the chemical compounds on the skin. However, some of the problems associated with conventional physical sunscreens include patchy appearance on the skin when higher concentrations are used. Further, most of the conventional physical sunscreens also have toxic effects on the skin due to release of reactive oxygen species by virtue of their photocatalytic properties.

SUMMARY

Embodiments of the present disclosure present technological improvements as solutions to one or more of the above-mentioned technical problems recognized by the inventors in the conventional sunscreen compositions.

In an aspect, a sunscreen composition containing visibly transparent biocompatible ultraviolet blocking polymer nanoparticles is provided. The sunscreen composition comprising polydimethylsiloxane (PDMS) nanoparticles, at least one flavoring agent, at least one coloring agent, at least one stabilizer, and at least one preservative, in a defined form, wherein size of the PDMS nanoparticles ranging from 200 to 1200 nm.

In an embodiment, the size of the PDMS nanoparticles ranging from 200 to 500 nm for air medium and 800 to 1200 nm for water medium.

In an embodiment, the PDMS nanoparticles comprise a PDMS polymer having terminal functional group selected from alkyl, alkoxy, vinyl, hydroxyl, or a combination thereof.

In an embodiment, the PDMS polymer is a cross-linked polymer.

In an embodiment, the PDMS nanoparticles provide attenuation from ultraviolet (UV) radiation in a wavelength range of 290-400 nm.

In an embodiment, the PDMS nanoparticles have an extinction co-efficient in the range of 100-200 $Lgm^{-1}$ $cm^{-1}$ in air medium under UV radiation in the wavelength range of 290-400 nm.

In an embodiment, the PDMS nanoparticles have an extinction co-efficient in the range of 20-50 $Lgm^{-1}$ $cm^{-1}$ in water medium under UV radiation in the wavelength range of 290-400 nm.

In an embodiment, the PDMS nanoparticles are UV filters.

In an embodiment, the defined form is selected from a group consisting of a skin cream, a skin lotion, a powder, a gel, and a sprayable liquid.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
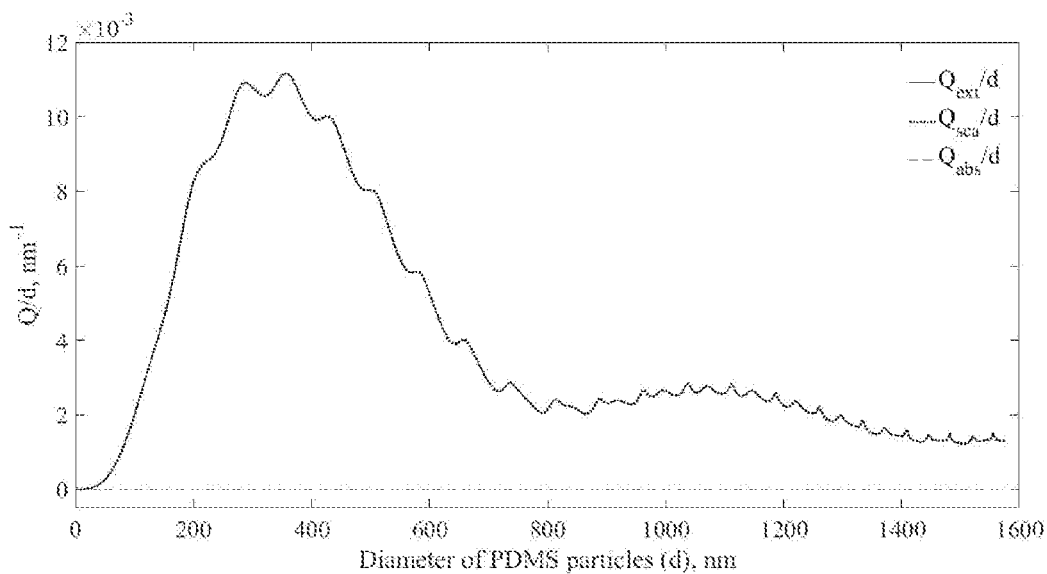
FIG. 1 is a graph showing a relative extinction efficiency ($Q_{ext}$/d), a relative scattering efficiency ($Q_{sca}$/d), and a relative absorption efficiency ($Q_{abs}$/d) of the PDMS nanoparticles in air medium, at varying size of the PDMS particles, in accordance with some embodiments of the present disclosure.
Figure 2:
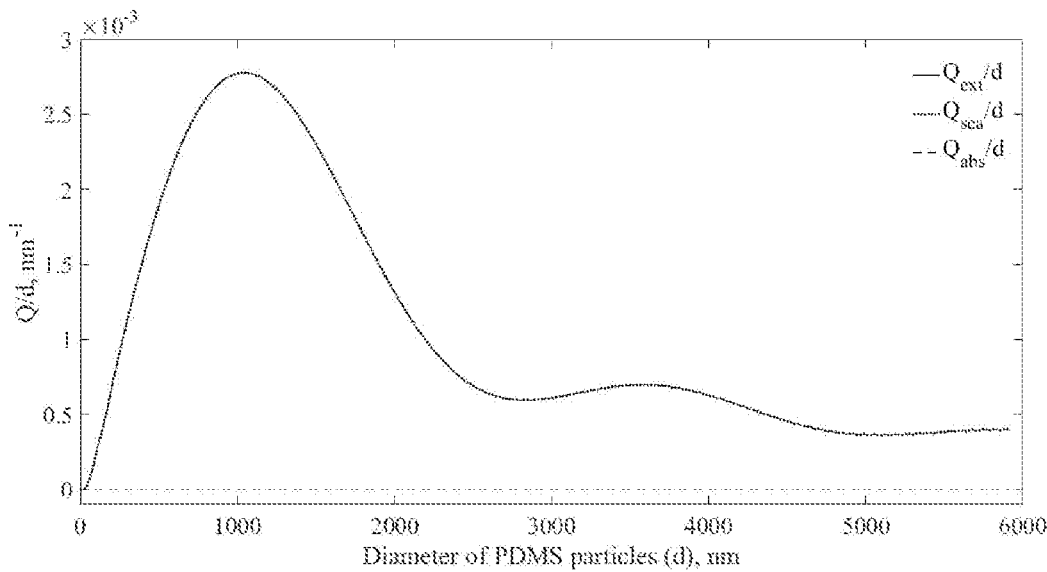
FIG. 2 is a graph showing a relative extinction efficiency ($Q_{ext}$/d), a relative scattering efficiency ($Q_{sca}$/d), and a relative absorption efficiency ($Q_{abs}$/d) of the PDMS nanoparticles in water medium, at varying size of the PDMS particles, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Ultraviolet (UV) radiation is a part of the solar spectrum with wavelengths ranging from 100 to 400 nm. A large part of the most damaging section of the ultraviolet radiation (UVC: 100-290 nm) is absorbed by the ozone layer in the atmosphere. However, a fraction of the radiation (UVB: 290-320 nm and UVA: 320-400 nm) penetrates the atmosphere and affects the skin of humans exposed to the sunlight. UVB radiation may cause redness of skin, sunburns, and increases the risk of basal cell and squamous cell carcinoma due to damage to the DNA of skin cells. UVA radiation may cause sun tanning, photoaging of the skin, and malignant melanomas due to indirect DNA damage by the generation of reactive free radicals. To prevent these problems, improved UV protection can be achieved through the use of UV attenuating materials such as physical and chemical sunscreens.

Chemical sunscreens are generally organic compounds that attenuate UV purely by absorption at the molecular level. On the other hand, physical sunscreens attenuate UV by mechanisms including scattering and reflection as well as absorption.

Further, chemical sunscreens are usually organic compounds which penetrate into the skin to varying extents. Studies indicate that most of the known chemical sunscreens made of the organic compounds have potentially toxic effects on skin cells. Prevalent physical sunscreens afford UV protection by means of a combination of scattering and absorption effects. They are usually metal oxides such as titanium dioxide ($TiO_2$) and zinc oxide (ZnO). Such compounds act as band-gap absorbers, absorbing UV photons due to the gap between the valence and conduction bands similar to semi-conductors. Such physical sunscreen materials, being naturally opaque, are undesirable as they leave white patches on the skin upon application at significant concentrations. A common strategy to overcome this problem is to reduce the size of the physical sunscreen material (particles) to the nano-range. However, the resulting metal oxide nanoparticles may easily penetrate through the skin and have high photocatalytic activity, releasing reactive oxygen species (ROSs) into the skin causing cell damage, accelerating skin aging, and potential carcinogenic effects. Further, the resulted metal oxide nanoparticles may not have natural adherent properties to the skin hence they are liable to be washed off easily and not effective over a long period of time.

Polydimethylsiloxane (PDMS) nanoparticles have potential to resolve many of the above issues by virtue of their inherent properties. PDMS is a non-toxic, biocompatible polymer that has been approved by the United States Food and Drug Administration (FDA) for topical and biomedical applications. PDMS has very strong adherent properties to skin and very similar mechanical and surface properties as skin. PDMS is also a visibly transparent and optically clear material which eliminates the possibility of unaesthetic patch formation on the skin.

Further, owing to the excellent biocompatibility of the PDMS nanoparticles, they have been explored in the past for anticancer drug delivery and developing functional skin tissues. All these properties make PDMS a superior alternative to existing sunscreens. However, they have not been utilized for developing sunscreen compositions before. To solve the above-mentioned problems, the present disclosure herein provides a novel sunscreen composition comprising PDMS nanoparticles which are visibly transparent biocompatible ultraviolet blocking (UV filter) polymer nanoparticles. The size of the PDMS nanoparticles is tuned for maximum UV attenuation. The standardized PDMS nanoparticles exhibit higher sun protection factor (SPF) even as compared to commercially available physical sunscreens.

In accordance with the embodiments of the present disclosure, the sunscreen composition includes PDMS nanoparticles, at least one flavoring agent, at least one coloring agent, at least one stabilizer, and at least one preservative, in a defined form. The size of the PDMS nanoparticles ranging from 200 to 1200 nm. In an embodiment, the size of the PDMS nanoparticles is tuned from 200 to 500 nm when the sunscreen composition is exposed to air medium, such that to achieve maximum UV attenuation. In another embodiment, the size of the PDMS nanoparticles is tuned from 800 to 1200 nm when the sunscreen composition is exposed to water medium, such that to achieve maximum UV attenuation.

In accordance with the embodiments of the present disclosure, the PDMS nanoparticles include a PDMS polymer, wherein the terminal functional group of the PDMS polymer is selected from alkyl, alkoxy, vinyl, hydroxyl, or a combination thereof. Further, the said PDMS polymer is a cross-linked polymer.

In accordance with the embodiments of the present disclosure, at least one flavoring agent is including in the sunscreen composition to get a flavoring effect. In an embodiment, at least one flavoring agent is selected from mints such as peppermint and menthol, cirrus flavors such as orange and lemon, vanilla, cinnamon, various other fruit flavors such as apple, mango, pineapple, and so on, both individual and mixed.

In accordance with the embodiments of the present disclosure, at least one coloring agent is including in the sunscreen composition. In an embodiment, at least one coloring agent is selected from pigments or dyes, or a combination thereof. In accordance with the embodiments of the present disclosure, at least one stabilizer is including in the sunscreen composition. In an embodiment, at least one stabilizer is selected from surfactants, emulsifiers, dispersants, detergents, or a combination thereof. Further, in accordance with the embodiments of the present disclosure, at least one preservative is including in the sunscreen composition. In an embodiment, at least one preservative is selected from antioxidants, vitamins, their derivatives, or a combination thereof.

In accordance with the embodiments of the present disclosure, a method of protecting skin from harmful UV radiation with an application of the said sunscreen composition is disclosed. The disclosed sunscreen composition may be commercially made in various defined forms for protecting the skin from harmful UV radiation. The defined form is selected from a group consisting of a skin cream, a skin lotion, a powder, a gel, a sprayable liquid, and so on. At least one flavoring agent, at least one coloring agent, at least one stabilizer, and at least one preservative, are thus chosen based on the defined form.

In accordance with the embodiments of the present disclosure, the PDMS nanoparticles provide attenuation from ultraviolet (UV) radiation in a wavelength range of 290-400 nm. The Mie theory is employed to measure the total attenuation of UV light by the disclosed PDMS nanoparticles. The total absorbance A (due to absorption and scattering) of a solution containing particles of radius r, number density N and path length l can be expressed in terms of extinction efficiency $Q_{ext}$ as, $$A = \frac{\pi r^2 Q_{ext} l N}{2.303} \quad (1)$$

The number density of particles N can be written as, $$N = c/(\rho V) \quad (2)$$

where, c is the concentration, $\rho$ is the density and V is the volume of particles. For spherical particles, $V=(4/3)\pi r^3$. Therefore, the total absorbance A may be further expressed as:

$$A = \frac{Q_{ext} l c}{1.535 \rho d} \quad (3)$$

where, d (=2r) is the diameter of the particles.
The extinction efficiency $Q_{ext}$ can be expressed using the Mie theory as, $$Q_{ext} = \frac{2}{x^2} \sum_{n=1}^{\infty} (2n+1) Re(a_n + b_n) \quad (4)$$

where, $a_n$ and $b_n$ are the Mie coefficients and function of m and x, $m = n_p/n_m$, where $n_p$ is the refractive index of the particles, $n_m$ is the refractive index of the surrounding medium, x is the size parameter ($x = 2\pi r n_m/\lambda$) and $\lambda$ is the wavelength. The scattering efficiency $Q_{sca}$ can be expressed as, $$Q_{sca} = \frac{2}{x^2} \sum_{n=1}^{\infty} (2n+1)(|a_n|^2 + |b_n|^2) \quad (5)$$

since $Q_{ext} = Q_{sca} + Q_{abs}$, absorption efficiency $Q_{abs}$ can be easily determined by subtracting $Q_{sca}$ from $Q_{ext}$. Numerical values of the above Mie efficiency parameters may be computed using the subroutine from Matzler's MATLAB functions.
The extinction coefficient (s) of the nanoparticles can be determined from total absorbance using Beer-Lambert law as, $$A = \varepsilon l c \quad (6)$$

Further, the SPF values may be determined from the absorbance values using the following equation, as demonstrated by Gubitosa et al., $$SPF_{Spectrophotometric} = CF \times \sum_{290}^{320} EE(\lambda) \times I(\lambda) \times Abs(\lambda) \quad (7)$$

where, $EE(\lambda)$ is the erythemal effect spectrum, $I(\lambda)$ is the solar intensity spectrum, $Abs(\lambda)$ is the absorbance and CF (=10) is the correction factor. The values of $EE(\lambda) \times I(\lambda)$ are constants and obtained from the reported data by Sayre et al.

In order to arrive at a particular size of the disclosed PDMS nanoparticles for maximum UV attenuation, a relative extinction efficiency is measured for varying diameter of the PDMS particles using the equation (4). The $n_p$ and $n_m$ values are obtained using an online database and as demonstrated by Herzog et al. All the calculations are performed considering incident irradiation at 310 nm wavelength since human skin exhibits maximum erythemal response upon exposure to this wavelength.

FIG. 1 is a graph showing a relative extinction efficiency ($Q_{ext}$/d), a relative scattering efficiency ($Q_{sca}$/d), and a relative absorption efficiency ($Q_{abs}$/d) of the PDMS nanoparticles in air medium, at varying size of the PDMS particles, in accordance with some embodiments of the present disclosure. As shown in FIG. 1, the PDMS nanoparticles having the size range from 300 to 400 nm exhibit higher extinction efficiency ($Q_{ext}$/d) values in air medium. More particularly from FIG. 1, the maximum relative extinction efficiency is observed when the size of the disclosed PDMS nanoparticles is 356 nm in the air medium. The relative scattering efficiency ($Q_{sca}$/d) values (computed using equation (5)) completely overlap with the relative extinction efficiency ($Q_{ext}$/d) values whereas the relative absorption efficiency ($Q_{ab}$s/d) values are almost negligible. This indicates that the observed extinction is entirely due to the scattering by the disclosed PDMS nanoparticles.

Similar calculations are performed for the disclosed PDMS nanoparticles in water medium. FIG. 2 is a graph showing a relative extinction efficiency ($Q_{ext}$/d), a relative scattering efficiency ($Q_{sca}$/d), and a relative absorption efficiency ($Q_{ab}$s/d) of the PDMS nanoparticles in water medium, at varying size of the PDMS particles, in accordance with some embodiments of the present disclosure. As shown in FIG. 2, the PDMS nanoparticles having the size range from 950 to 1100 nm exhibit higher extinction efficiency ($Q_{ext}$/d) values in water medium. More particularly from FIG. 2, the maximum relative extinction is achieved for the PDMS nanoparticles of 1042 nm diameter. Also, contribution from the relative absorption to overall relative extinction is negligible. Since the PDMS nanoparticles of 356 nm and 1042 nm size exhibit maximum attenuation of UV light (310 nm) in the air medium and the water medium, respectively, these PDMS nanoparticles of the said size are only considered for further studies in respective mediums.

FIG. 3A is a graph showing a comparison of the extinction coefficients of the PDMS nanoparticles having size of 356 nm, with conventional sunscreen nanoparticles, in air medium, in accordance with some embodiments of the present disclosure. FIG. 3B is a graph showing a comparison of the extinction coefficients of the PDMS nanoparticles having size of 1042 nm, with conventional sunscreen nanoparticles, in water medium, in accordance with some embodiments of the present disclosure. The conventional sunscreen nanoparticles considered as $TiO_2$ and ZnO having particle size of 15 nm and 30 nm, respectively. As shown in FIG. 3A and FIG. 3B, the maximum extinction coefficient is observed in UVA and UVB regions for both sizes (356 nm and 1042 nm) of the PDMS nanoparticles in respective medium. Most importantly, higher extinction coefficient values are achieved by the PDMS nanoparticles as compared to the commercial sunscreen nanoparticles $TiO_2$ and ZnO.

From FIG. 3A and FIG. 3B, the PDMS nanoparticles have an extinction co-efficient in the range of 100-200 $Lgm^{-1}$ cm$^{-1}$ in air medium under UV radiation in the wavelength range of 290-400 nm. The PDMS nanoparticles have an extinction co-efficient in the range of 20-50 Lgm$^{-1}$ cm$^{-1}$ in water medium under UV radiation in the wavelength range of 290-400 nm. Moreover, the PDMS nanoparticles exhibit low extinction in the visible range as compared to UV range, indicating visible transparency of the nanoparticles desirable for the sunscreen composition applications.

Figure 3A:
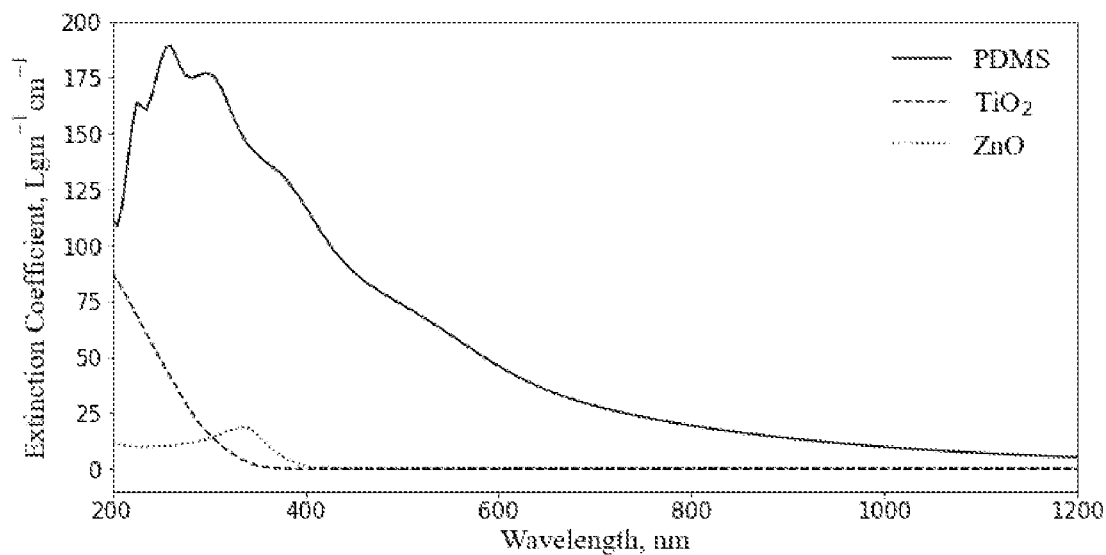
FIG. 3A is a graph showing a comparison of the extinction coefficients of the PDMS nanoparticles having size of 356 nm, with conventional sunscreen nanoparticles, in air medium, in accordance with some embodiments of the present disclosure.
Figure 3B:
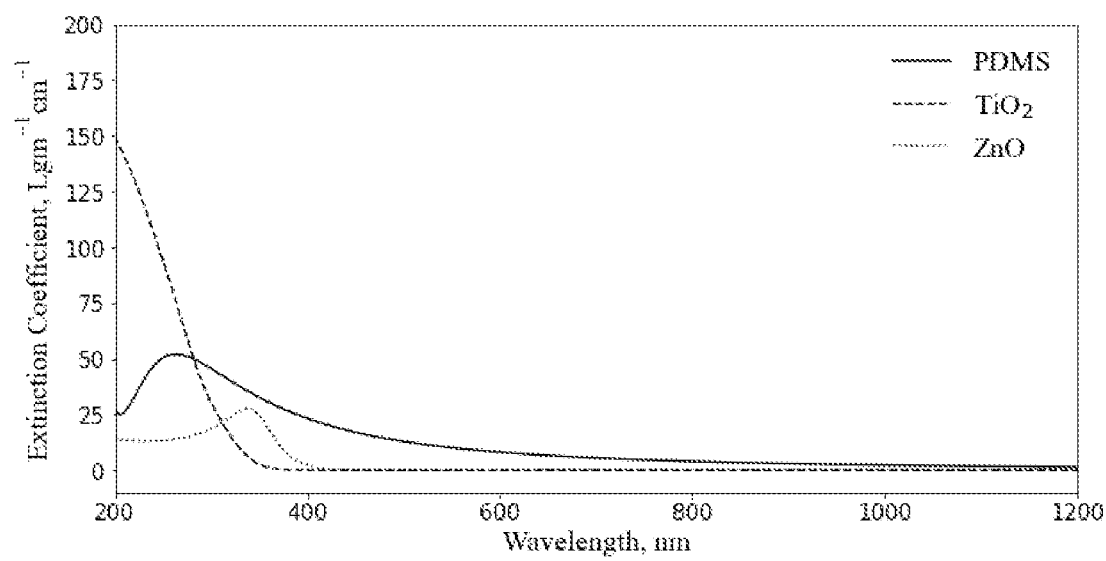
FIG. 3B is a graph showing a comparison of the extinction coefficients of the PDMS nanoparticles having size of 1042 nm, with conventional sunscreen nanoparticles, in water medium, in accordance with some embodiments of the present disclosure.

The extinction coefficient values resulted from FIG. 3A and FIG. 3B are used to measure the total absorbance (scattering plus absorption) of the disclosed PDMS nanoparticles and the conventional sunscreen nanoparticles TiO$_2$ and ZnO for concentration (c) of 0.005 wt % and path length (l) of 1 cm using equation (6).

Figure 4A:
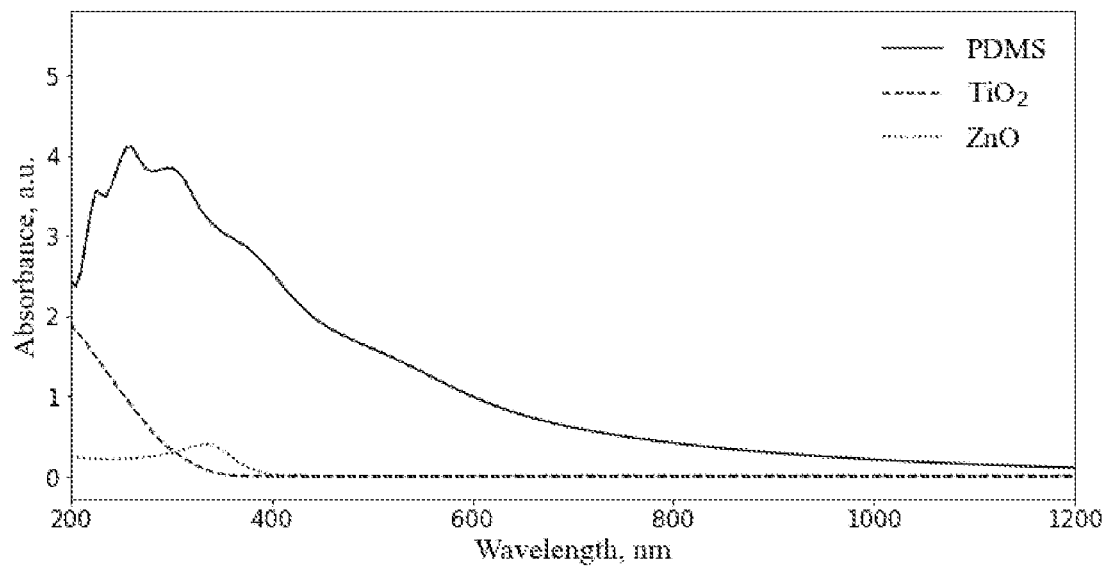
FIG. 4A is a graph showing a comparison of a total absorbance of the PDMS nanoparticles having size of 356 nm, with conventional sunscreen nanoparticles, in air medium, in accordance with some embodiments of the present disclosure.
Figure 4B:
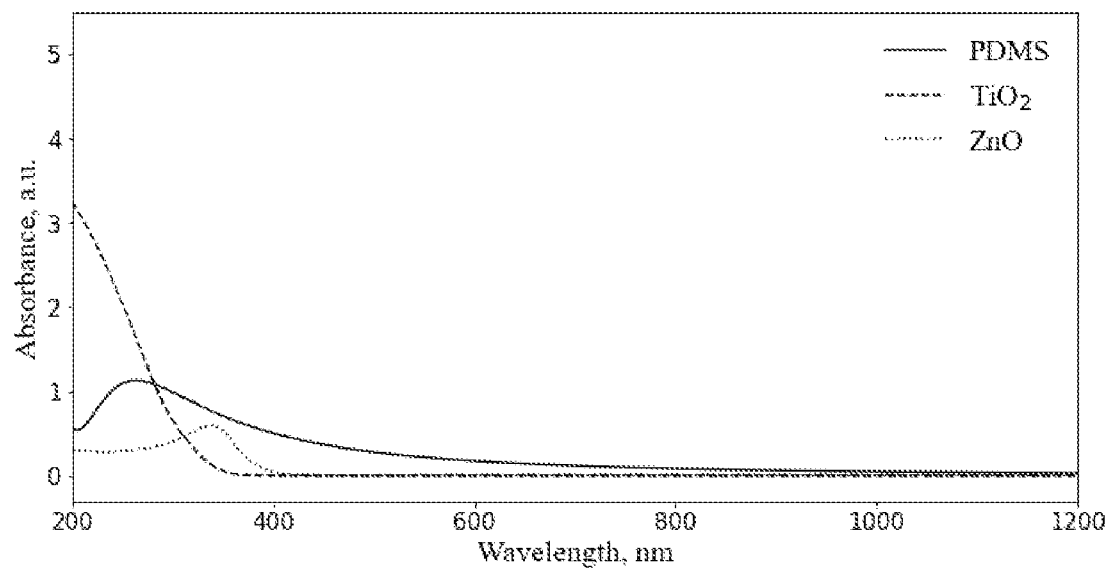
FIG. 4B is a graph showing a comparison of a total absorbance of the PDMS nanoparticles having size of 1042 nm, with conventional sunscreen nanoparticles, in water medium, in accordance with some embodiments of the present disclosure.

FIG. 4A is a graph showing a comparison of a total absorbance of the PDMS nanoparticles having size of 356 nm, with conventional sunscreen nanoparticles, in air medium, in accordance with some embodiments of the present disclosure. FIG. 4B is a graph showing a comparison of a total absorbance of the PDMS nanoparticles having size of 1042 nm, with conventional sunscreen nanoparticles, in water medium, in accordance with some embodiments of the present disclosure. As shown in FIG. 4A and FIG. 4B, the total absorbance values of the disclosed PDMS nanoparticles in the UVA and UVB regions are significantly higher as compared to the conventional sunscreen nanoparticles TiO$_2$ and ZnO in both air medium and water medium, respectively.

The most traditionally accepted approach for evaluating the efficiency of the sunscreen composition is based on sun protection factor (SPF) measurement. The SPF value of the sunscreen composition represents a quantitative measure for the amount of protection from harmful UV irradiation. Therefore, the absorbance values obtained from FIG. 4A and FIG. 4B are utilized to compute SPF values of the nanoparticles using equation (7).

Figure 5:
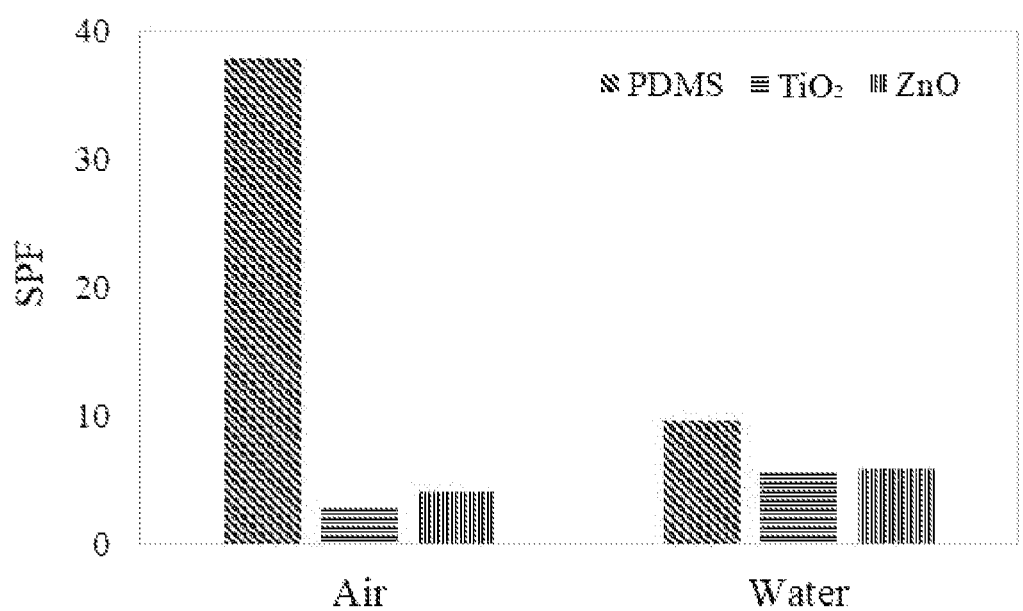
FIG. 5 is a graph showing a comparison of a sun protection factor (SPF) of the PDMS nanoparticles, with conventional sunscreen nanoparticles, in air medium and water medium, respectively, in accordance with some embodiments of the present disclosure.

FIG. 5 is a graph showing a comparison of a sun protection factor (SPF) of the PDMS nanoparticles, with conventional sunscreen nanoparticles, in air medium and water medium, respectively, in accordance with some embodiments of the present disclosure. The PDMS nanoparticles having size of 356 nm is considered for air medium and the size of 1042 nm is considered for water medium. As shown in FIG. 5, the PDMS nanoparticles exhibit SPF of 38 and 10 in air medium and water medium, respectively, much higher than the corresponding SPF values of the conventional sunscreen nanoparticles such as TiO$_2$ and ZnO. Hence, from the study and analysis, the disclosed PDMS nanoparticles of appropriate size range possess higher UV protection capability than commercial conventional sunscreen nanoparticles.

Also, the UV extinction properties of the disclosed PDMS nanoparticles in air medium have been consistently higher than the corresponding values in water medium. Therefore, the disclosed PDMS nanoparticles may be more useful for spray-based sunscreen applications than in the form of aqueous dispersion. Thus, based on the results, the disclosed PDMS nanoparticles exhibit excellent UV blocking properties and otherwise called as UV filters.

In accordance with the present disclosure, the sunscreen composition is made up of polydimethylsiloxane (PDMS) nanoparticles which are transparent, biocompatible, safe, non-toxic and UV blocking polymer nanoparticles. Since, the PDMS is well known to be biocompatible, it may be used in biomedical applications. PDMS is also FDA approved for use in cosmetics as well as internal implants in biomedical uses.

Since the polydimethylsiloxane (PDMS) nanoparticles are transparent, the disclosed sunscreen composition eliminates the problem of patchy appearance on the skin because PDMS is fundamentally visibly clear and transparent. The results show that the PDMS nanoparticles used in the disclosed composition have a high extinction coefficient in the UV region and very low extinction in the visible region which implies that they have high degree of UV protection but leave no visible residues when applied on the skin or skin surfaces. Further, the disclosed PDMS nanoparticles of appropriate size range possess higher UV protection capability than commercial conventional sunscreen nanoparticles such as TiO$_2$ and ZnO.

The PDMS nanoparticles exhibit higher SPF than the corresponding SPF values of the conventional sunscreen nanoparticles such as TiO$_2$ and ZnO. The disclosed sunscreen composition consisting of standalone PDMS nanoparticles, is long lasting and durable on the skin after application because PDMS naturally shows a high degree of adhesion to skin as one of its properties.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope of disclosed embodiments being indicated by the following claims.

What is claimed is:

1. A sunscreen composition comprising polydimethylsiloxane (PDMS) nanoparticles, at least one flavoring agent, at least one coloring agent, at least one stabilizer, and at least one preservative, wherein the sunscreen composition is present in a defined form and size of the PDMS nanoparticles ranging from 200 to 1200 nm.

2. The sunscreen composition of claim 1, wherein the size of the PDMS nanoparticles ranging from 200 to 500 nm for air medium and 800 to 1200 nm for water medium.

3. The sunscreen composition of claim 1, wherein the size of the PDMS nanoparticles ranging from 300 to 400 nm for air medium and 950 to 1100 nm for water medium.

4. The sunscreen composition of claim 1, wherein the PDMS nanoparticles comprise a PDMS polymer having terminal functional group selected from alkyl, alkoxy, vinyl, hydroxyl, or a combination thereof.

5. The sunscreen composition of claim 3, wherein the PDMS polymer is a cross-linked polymer.

6. The sunscreen composition of claim 1, wherein the PDMS nanoparticles provide attenuation from ultraviolet (UV) radiation in a wavelength range of 290-400 nm.

7. The sunscreen composition of claim 1, wherein the PDMS nanoparticles have an extinction co-efficient in the range of 100-200 $Lgm^{-1}$ $cm^{-1}$ in air medium under UV radiation in the wavelength range of 290-400 nm.

8. The sunscreen composition of claim 1, wherein the PDMS nanoparticles have an extinction co-efficient in the range of 20-50 $Lgm^{-1}$ $cm^{-1}$ in water medium under UV radiation in the wavelength range of 290-400 nm.

9. The sunscreen composition of claim 1, wherein the PDMS nanoparticles are UV filters.

10. The sunscreen composition of claim 1, wherein the defined form is selected from a group consisting of a skin cream, a skin lotion, a powder, a gel, and a sprayable liquid.

11. A method of protecting skin from harmful UV radiation with an application of a sunscreen composition according to claim 1.

* * * * *